US00PP30420P3

(12) United States Plant Patent
Kordes

(10) Patent No.: US PP30,420 P3
(45) Date of Patent: Apr. 23, 2019

(54) MINIATURE ROSE PLANT NAMED 'KORAROMA07'

(50) Latin Name: *Rosa hybrida*
Varietal Denomination: KORaroma07

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 16 days.

(21) Appl. No.: 15/731,500

(22) Filed: Jun. 20, 2017

(65) Prior Publication Data

US 2017/0374772 P1 Dec. 28, 2017

Related U.S. Application Data

(60) Provisional application No. 62/493,172, filed on Jun. 23, 2016.

(51) Int. Cl.
*A01H 5/02* (2018.01)
*A01H 6/74* (2018.01)

(52) U.S. Cl.
USPC ..... Plt./121
CPC ..... *A01H 5/02* (2013.01); *A01H 6/749* (2018.05)

(58) Field of Classification Search
USPC ..... Plt./121
See application file for complete search history.

*Primary Examiner* — Anne Marie Grunberg
(74) *Attorney, Agent, or Firm* — Samuel R. McCoy, Jr.

(57) ABSTRACT

'KORaroma07' is a new and distinct variety of *Rosa hybrida* plant which is characterized by the combination of a compact and bushy growth habit with a moderately vigorous rate of growth, above average resistance to many rose diseases, pink flowers borne solitarily and in racemes of 2 to 5 flowers, double flowers, and flowers with a moderately strong myrrh and floral perfume. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORaroma07'.

STATEMENT REGARDING PRIOR DISCLOSURES BY THE INVENTOR UNDER 37 C.F.R. 1.77(B)(6)

The first public disclosure of the claimed plant was made in January of 2016 at the 2016 IPM horticulture tradeshow in Essen, Germany where it was displayed by the inventor amongst a collection of other rose cultivars. The claimed plant was not specifically identified by name in the display. 'KORaroma07' was not publically available or sold prior to one year before the date of the instant application.

BACKGROUND OF THE INVENTION

Parentage: The *Rosa hybrida* variety 'KORaroma07' is the result of a controlled cross-pollination breeding program carried out by the inventor in Klein Offenseth-Sparrieshoop, Germany. The objective of the said breeding program was to create a new and distinct rose plant with unique qualities, such as:

1. A compact growth habit and uniform flowering when grown as a potted floral plant; and
2. Long-lasting, fragrant and recurrent pink flowers; and
3. Attractive foliage; and 4. Resistance to diseases encountered in greenhouse production.

This combination of qualities is not present in prior rose cultivars known to the inventor. These objectives have been substantially achieved and in that distinguish 'KORaroma07' from all other varieties known to the inventor.

'KORaroma07' is a seedling selection which resulted from the controlled pollination of an unnamed *Rosa hybrida* seedling developed and owned by the same inventor, the seed parent, with *Rosa hybrida* 'KORnilsca' (U.S. Plant Pat. No. 16,268), the pollen parent, during the summer of 2013. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2014 from the seedling beds due to its superior characteristics and asexually propagated for further evaluation. This new and distinctive rose variety was given the name 'KORaroma07'.

Asexual Reproduction: 'KORaroma07' was first asexually propagated by rooting vegetative cuttings in June of 2014 at the inventor's nursery in Klein Offenseth-Sparrieshoop, Germany. Subsequently, 'KORaroma07' has been successfully propagated by stem cuttings in Jackson County, Oreg. These initial and other subsequent propagations conducted in controlled environments demonstrate that 'KORaroma07' reproduces true to type in successive generations of asexual reproduction.

SUMMARY OF THE INVENTION

The following characteristics have been repeatedly observed and represent the distinguishing characteristics of the new *Rosa hybrida* cultivar 'KORaroma07'. These traits, in combination, distinguish 'KORaroma07' as a new and distinct cultivar.

1. *Rosa hybrida* 'KORaroma07' exhibits a moderately vigorous growth rate; and
2. *Rosa hybrida* 'KORaroma07' exhibits a compact and bushy growth habit; and
3. *Rosa hybrida* 'KORaroma07' exhibits above average resistance to powdery mildew and *Botrytis* diseases; and
4. *Rosa hybrida* 'KORaroma07' exhibits pink flowers borne both solitarily and in racemes of 2 to 5 flowers; and
5. *Rosa hybrida* 'KORaroma07' exhibits double flowers that are held upright; and
6. *Rosa hybrida* 'KORaroma07' exhibits flowers with moderately strong myrrh and floral perfume.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORaroma07', taken from a 15 month old plant.

DETAILED BOTANICAL DESCRIPTION

The following is a detailed botanical description of a new and distinct variety of *Rosa hybrida* known as 'KORaroma07', based upon observations made in May of 2017 from 15 month old, greenhouse-grown container plants in Jackson County, Oreg. Those skilled in the art will appreciate that certain characteristics will vary with older or, conversely, with younger plants. 'KORaroma07' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition except where common terms of color are used.

A botanical description of 'KORaroma07' and comparisons with the parents and closest known comparator variety of *Rosa hybrida* are provided below.

General plant description:

*Growth rate.*—Moderately vigorous.

*Growth habit.*—Compact and bushy.

*Mature dimensions.*—30 to 40 cm tall and 18 to 22 cm wide, when grown as a 15 cm pot plant.

*Cold hardiness.*—Unknown.

*Propagation.*—Stem cuttings and bud grafting.

*Disease resistance.*—Above average resistance to powdery mildew (*Sphaerotheca pannosa*) and *Botrytis* sp. diseases under normal greenhouse growing conditions in Jackson County, Oreg.

Root system:

*Type.*—Fibrous root system, with many root hairs.

*Branching.*—Moderately branched.

*Density.*—Moderately dense.

*Distribution.*—Roots distributed evenly throughout the soil profile, from shallow to deep.

Stems:

*Stem color.*—Young stems are Yellow-Green Group 147A; mature stems are Yellow-Green Group 147A.

*Anthocyanin intonations.*—Intonations of Greyed-Purple Group 183C are present on the juvenile and young stems.

*Stem surface texture.*—Both juvenile stems and mature stems are smooth.

*Stem dimensions.*—Typical mature stems are approximately 15 to 18 cm long and 4.0 to 8.0 mm in diameter.

*Prickles.*—Incidence — Typically 6 to 8 prickles per 10 cm of stem, on average. Size — Average length is 3.0 to 4.0 mm long. Immature prickle color — Greyed-Purple Group 184D. Mature prickle color — Greyed-Purple Group 182C and suffused with Greyed-Purple Group 183C. Shape — Linear. Texture — Smooth.

Leaves:

*Arrangement.*—Imparipinnate compound leaves; mature axillary leaves typically with 5 to 7 leaflets on normal leaves in the middle of the stems; leaves with 7 leaflets are more common on longer stems.

*Attachment.*—Petiolate.

*Dimensions.*—140 mm long and 70 mm wide.

*Abundance.*—Very abundant; normally with 30 to 40 leaves.

*Stipules.*—Size — 18 mm long and 7.0 mm wide. Stipule color — Yellow-Green Group 147B. Anthocyanin intonations — Greyed-Purple Group 183C, mostly present on the adaxial surface; light suffusion with Greyed-Purple Group 183C on the abaxial surface. Stipitate glands — Abundant along the margins. Margins — With stipitate glands. Texture, adaxial surfaces — Glabrous; leathery. Texture, abaxial surfaces — Glabrous; smooth. Apex — Apiculate. Base — Winged.

*Petiole.*—Length — Average 15 mm. Diameter — Average 1.5 mm. Petiole color, adaxial surface — Yellow-Green Group 147B. Petiole color, abaxial surface — Yellow-Green Group 147B. Anthocyanin intonations — Greyed-Purple Group 183C. Margins — With a moderate number of stipitate glands. Prickles — A few short prickles on the abaxial surface. Stipitate glands — Moderate number of stipitate glands are present. Texture — Glabrous. Strength — Strong.

*Rachis.*—Length — Average 15 mm. Diameter — Average 1.5 mm. Color — Yellow-Green Group 147B. Anthocyanin intonations — Greyed-Purple Group 183C. Margins — With a moderate number of stipitate glands. Prickles — None. Stipitate glands — A moderate number of stipitate glands are present. Texture — Glabrous.

*Leaflets.*—Dimensions — Average size of the terminal leaflet is 32 mm long and 45 mm wide. Shape — Elliptic. Apex — Acute. Base — Obtuse. Margins — Finely serrated; no undulation. Texture, pubescence, and luster; adaxial surface — Leathery, glabrous, and semi-glossy. Texture, pubescence, and luster; abaxial surface — Leathery, glabrous, and matte. Stipitate glands — A limited number of stipitate glands are present along the abaxial midrib and margins. Juvenile foliage color, adaxial surface — Green Group 137A. Juvenile foliage color, abaxial surface — Green Group 138A. Mature foliage color, adaxial surface — Green Group 137A. Mature foliage color, abaxial surface — Green Group 138A. Anthocyanin intonations — Strong intonations of Greyed-Purple Group 183C are present on both the adaxial and abaxial surfaces of the juvenile foliage and also the margins of mature foliage. Venation — Reticulate. Petiolule — Dimensions — 2.0 to 3.0 mm long and 1.0 mm in diameter. Petiolule color, adaxial surface — Yellow-Green Group 147B. Petiolule color, abaxial surface — Yellow-Green Group 147B. Anthocyanin intonations — Strong intonations of Greyed-Purple Group 183C are present on both the adaxial and abaxial surfaces of the juvenile foliage. Prickles — Present on the abaxial surface. Margins — Entire. Texture, adaxial surface — Leathery. Texture, abaxial surface — Smooth.

Inflorescence:

*Inflorescence type.*—Flowers are both solitary and borne on racemes of 2 to 5 flowers, with flowers at the center of the inflorescence blooming first. Flowers are held upright.

*Blooming habit.*—Recurrent; floriferous.

*Size.*—80 mm tall and 40 mm wide, on average.

*Peduncle.*—Length — 20 to 40 mm average length. Diameter — 5.0 to 7.0 mm average diameter. Color — Green Group 138A. Anthocyanin intonations — Greyed-Purple Group 183C; intonations diminishing as flower buds open. Strength — Strong. Surface — Glabrous.

Flowering laterals: Absent.

Flower bud:

*Bud form.*—Long; pointed ovoid.

*Size.*—Upon opening, 50 mm in length from base of receptacle to distal end of bud and 22 mm diameter at its widest point.

*Texture.*—Smooth.

*Color, as sepals first unfold.*—Red-Purple Group 58A.

*Color when one-quarter open, inner side.*—Marginal Zone — Red-Purple Group 58B. Middle Zone — Red-Purple Group 58B. Basal Zone — Red-Purple Group 58B.

*Color when one-quarter open, outer side.*—Marginal Zone — Red-Purple Group 63B. Middle Zone — Red-Purple Group 63B. Basal Zone — Red-Purple Group 63A.

*Color, outermost petals.*—Red-Purple Group 58A, and suffused with White Group N155B at the base and along the midrib.

Flower:

*Pedicels.*—Length — 25 to 35 mm average length. Diameter — 3.0 to 4.0 mm average diameter. Color — Green Group 138A. Anthocyanin intonations — Greyed-Purple Group 183C; intonations diminishing as flower open. Strength — Strong. Surface — Lightly pubescent.

*Calyx.*—General — Comprised of five polysepalous sepals, with strong foliaceous appendages present on three sepals. Diameter of calyx — 70 mm, at anthesis. Sepals — Color, upper surface — Green Group 137A. Color, lower surface — Green Group 138A. Anthocyanin intonations — Greyed-Purple Group 183C. Size — 25 mm long and 8.0 to 10 mm wide, on average. Apex — Cirrose. Base — Flat at union with receptacle. Quantity — Five. Upper surface — Smooth; glabrous. Lower surface — Pubescent. Margins — Entire; limited number of stipitate glands are present. Stipitate glands, occurrence — Limited.

*Corolla.*—Conformation — Double. General shape of corolla — Round. Shape of corolla when viewed from the side — Upon opening, upper portion — Flattened convex. Upon opening, lower portion — Flat. Open flower, upper portion — Flattened convex. Open flower, lower portion — Flat. Dimensions — Medium size for a miniature rose. When open, the average flower diameter is 60 to 65 mm and the average flower height is 50 mm. Fragrance — Moderate myrrh and floral perfume. Duration — On the plant for 12 to 16 days. Senesced petals clinging. Petals — Petal count — Exhibits double flowers with an average of 33 petals under normal conditions. Petal reflex — Petals are slightly reflexed. Timing of petal reflex — One by one. Petal margin — Entire; not undulated. Petal shape — Nearly round. Apex — Obtuse with a short mucronate tip. Base — Obtuse. Dimensions — 40 mm long and 40 mm wide. Texture, inner surface — Smooth. Texture, outer surface — Smooth. Petal color, upon opening — Outermost petals, inner surface — Marginal Zone — Red-Purple Group N66B. Middle Zone — Red-Purple Group N66B. Basal Zone — Red-Purple Group N66A. Outermost petals, outer surface — Marginal Zone — Red-Purple Group 63B. Middle Zone — Red-Purple Group 63B. Basal Zone — Red-Purple Group 63A. Innermost petals, inner surface — Marginal Zone — Red-Purple Group N66B. Middle Zone — Red-Purple Group N66A. Basal Zone — Red-Purple Group N66A. Innermost petals, outer surface — Marginal Zone — Red-Purple Group 63B. Middle Zone — Red-Purple Group 63A. Basal Zone — Red-Purple Group 63A. Basal petal spots, upon opening — Outermost petals — Color, inner surface — Yellow Group 3D. Color, outer surface — Yellow-White Group 158D. Dimensions — 5 mm wide and 8 mm tall. Innermost petals — Color, inner surface — Yellow Group 3B. Color, outer surface — Yellow-White Group 158D. Dimensions — 5 mm wide and 8 mm tall. Petal color, after opening — Outermost petals, inner surface — Marginal Zone — Red-Purple Group N66B. Middle Zone — Red-Purple Group N66B. Basal Zone — Red-Purple Group N66A. Outermost petals, outer surface — Marginal Zone — Red-Purple Group 63B. Middle Zone — Red-Purple Group 63B. Basal Zone — Red-Purple Group 63A. Innermost petals, inner surface — Marginal Zone — Red-Purple Group N66B. Middle Zone — Red-Purple Group N66A. Basal Zone — Red-Purple Group N66A. Innermost petals, outer surface — Marginal Zone — Red-Purple Group 63B. Middle Zone — Red-Purple Group 63A. Basal Zone — Red-Purple Group 63A. Basal petal spots, after opening — Outermost petals — Color, inner surface — Yellow Group 3D. Color, outer surface — Yellow-White Group 158D. Dimensions — 5 mm wide and 8 mm tall. Innermost petals — Color, inner surface — Yellow Group 3D. Color, outer surface — Yellow-White Group 158D. Dimensions — 5 mm wide and 8 mm tall. General Tonality — On open flower, Red-Purple Group N66B. No change in general tonality at the end of the tenth day; thereafter the general tonality is Red-Purple Group N66C.

*Petaloids.*—Quantity — 11 to 12 petaloids per flower, on average. Dimensions — Variable; 30 mm long and 20 mm wide on average. Color, inner surface — Marginal Zone — Red-Purple Group N66B. Middle Zone — Red-Purple Group N66A. Basal Zone — Red-Purple Group N66A. Color, outer surface — Marginal Zone — Red-Purple Group 63B. Middle Zone — Red-Purple Group 63A. Basal Zone — Red-Purple Group 63A. Margins — Entire; slightly undulated. Shape — Variable but generally ovate. Apex — Acute Base — Obtuse. Texture, inner and outer surfaces — Smooth.

Reproductive organs:

*Stamens.*—Quantity — Approximately 100, on average, arranged around the styles. Anthers — Shape — Reniform. Dimensions — 2.0 to 3.0 mm long and 1.0 to 1.5 mm wide, on average. Color — Greyed-Orange Group 163B. Pollen color — Yellow-Orange Group 14C. Filaments — Color — Yellow Group 2B; innermost filaments are occasionally suffused with Greyed-Purple Group 185D. Length — 3.0 to 6.0 mm.

*Pistils.*—Quantity — Abundant; approximately 90. Stigmas — Size — 1.0 mm long and 1.0 mm wide. Location — Slightly inferior in position to anthers. Color — Greyed-Yellow Group 160C. Styles — Length — Approximately 6.0 to 10 mm long. Color — White Group 155A, with intonations of Red-Purple Group 63B. Ovary — Dimensions — 14 mm long and 9.0 mm in diameter. Color — Green-White Group 157C.

*Receptacle.*—Shape — Urn-shaped. Dimensions — Approximately 9.0 to 11 mm high and 13 to 14 mm wide. Color — Yellow-Green Group 146C, with Greyed-Purple Group 183C intonations. Texture — Rugose and lightly pubescent.

Hips and seed formation: Not observed.

Comparison with the Parents

The new rose plant may be distinguished from its seed parent, an unnamed *Rosa hybrida* seedling, by the following combination of characteristics:

1. 'KORaroma07' exhibits double flowers, whereas the seed parent exhibits semi-double flowers.
2. 'KORaroma07' exhibits medium flowers for a miniature rose, whereas the seed parent exhibits larger flowers.
3. 'KORaroma07' exhibits a moderately long shelf life as a potted plant, whereas the pollen parent exhibits a short shelf life as a potted plant.

The new rose plant may be distinguished from its pollen parent, *Rosa hybrida* 'KORnilsca' (U.S. Plant Pat. No. 16,268), by the following combination of characteristics:

1. 'KORaroma07' exhibits a compact and bushy growth habit, whereas the pollen parent exhibits an upright to bushy growth habit.
2. 'KORaroma07' exhibits medium sized flowers for a miniature rose, whereas the pollen parent exhibits smaller flowers.
3. 'KORaroma07' exhibits flowers with moderately strong myrrh and floral perfume, whereas the flowers of the pollen parent exhibit a light fragrance.

Comparison with the Most Similar *Rosa* Cultivar Known to the Inventor

For a comparison, several physical characteristics of the *Rosa hybrida* variety 'KORpot066', a rose variety from the same inventor which is described and illustrated in U.S. Plant Pat. No. 29,702, are compared to 'KORaroma07' in Chart 1.

CHART 1

| Characteristic | 'KORaroma07' | 'KORpot066' |
|---|---|---|
| Diameter of flower, at anthesis. | 60 to 65 mm. | 45 to 55 mm. |
| General tonality of the flower, at anthesis. | Red-Purple Group N66B. | Red-Purple Group 57A. |
| Flower bud size upon opening. | 50 mm long and 22 mm wide, at the widest point. | 28 mm long and 17 mm wide, at the widest point. |
| Fragrance. | Moderately strong, myrrh and floral perfume. | Light floral fragrance. |

That which is claimed:

1. A new and distinct variety of rose plant named 'KORaroma07', as described and illustrated herein.

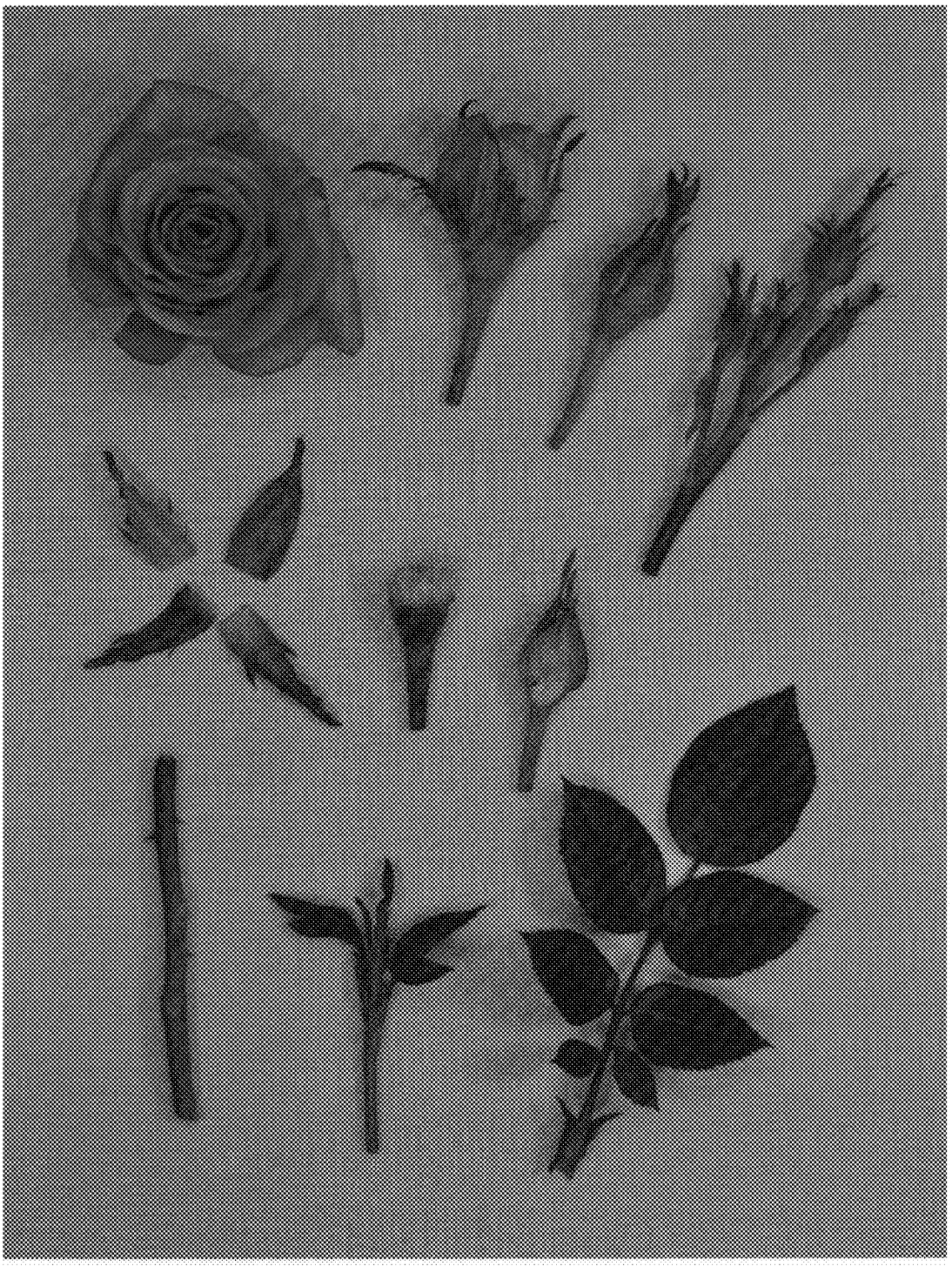

* * * * *